(12) United States Patent
Egalon

(10) Patent No.: US 6,282,338 B1
(45) Date of Patent: Aug. 28, 2001

(54) INTERFACIAL PROPAGATING MODE WAVEGUIDE

(75) Inventor: Claudio O. Egalon, Torrance, CA (US)

(73) Assignee: Intelligent Optical Systems, Inc., Torrance, CA (US)

(*) Notice: Subject to any disclaimer, the term of this patent is extended or adjusted under 35 U.S.C. 154(b) by 0 days.

(21) Appl. No.: 09/495,181

(22) Filed: Feb. 1, 2000

(51) Int. Cl.[7] .................................................. G02B 6/26
(52) U.S. Cl. ........................................... 385/28; 385/37
(58) Field of Search ................................. 385/1, 16, 37, 385/43, 2; 372/6, 69, 70, 71; 356/32, 33; 359/130, 124, 127

(56) References Cited

U.S. PATENT DOCUMENTS

| | | | |
|---|---|---|---|
| 5,082,349 | * | 1/1992 | Cordova-Plaza et al. ............... 385/2 |
| 5,185,749 | * | 2/1993 | Kalman et al. ........................... 372/6 |
| 5,627,637 | * | 5/1997 | Kapteyn .................................. 385/43 |
| 5,805,751 | * | 9/1998 | Kewitsch et al. ...................... 356/37 |
| 5,875,272 | * | 2/1999 | Kewitsch et al. ...................... 385/37 |
| 5,903,686 | * | 5/1999 | Lowry ..................................... 385/1 |
| 5,937,115 | * | 8/1999 | Domash ................................. 385/16 |
| 6,078,709 | * | 6/2000 | Abramov et al. ...................... 385/37 |
| 6,201,909 | * | 3/2000 | Kewitsch et al. ...................... 385/37 |

\* cited by examiner

*Primary Examiner*—Akm E. Ullah
(74) *Attorney, Agent, or Firm*—Herbert M. Shapiro

(57) ABSTRACT

An optical fiber waveguide including a selected period reflection grating structure for coupling the forward propagating mode of an optical signal transmitted through the waveguide into a backward propagating interfacial mode where a substantial portion of the optical signal is propagated in the cladding region of the fiber.

8 Claims, 3 Drawing Sheets

CHARACTERISTICS

| BOUND MODES | IPMs |
|---|---|
| $n_{core} > n_{eff} > n_{clad}$ | $n_{eff} > n_{core}$ |
| PEAK POWER AT THE CENTER OF THE WAVEGUIDE | PEAK POWER IS AT THE CORE/CLADDING INTERFACE |
| POWER DISTRIBUTED THROUGHOUT THE CORE | HIGH POWER DENSITY AT THE CORE/CLADDING BOUNDARY |

INTERFACIAL PROPAGATING MODE WAVEGUIDE

CROSS-REFERENCE TO RELATED APPLICATIONS

Not Applicable

FEDERALLY SPONSORED RESEARCH OR DEVELOPMENT

Not Applicable

FIELD OF THE INVENTION

The present invention relates generally to the propagation of light in optical waveguides and more particularly to an interfacial propagating mode in an optical fiber waveguide.

BACKGROUND OF THE INVENTION

Optical fiber waveguides are being used with increasing regularity for the transmission and processing of optical signals. In addition to telecommunications applications, fiber optic sensors are used for measuring parameters such as temperature, pressure, radiation levels, chemical concentrations and the like. In an optical fiber sensor, for example, having a core and a surrounding cladding, the presence of chemical analytes can produce a change in the refractive indices of the cladding and core and consequently in the optical output of the fiber. A need exists, however, for improved optical fiber sensors that are more sensitive and that can produce greater variations in optical output.

BRIEF SUMMARY OF THE INVENTION

The present invention comprises an optical fiber waveguide for generating a new type of light propagating mode, an interfacial propagating mode (IPM), where a substantial portion of light energy transmitted through the waveguide is propagated in the cladding region of the fiber. Furthermore, by increasing the amount of light transmitted through the cladding, higher amounts of fluorescence in the cladding can be excited and more light absorption can be achieved to produce more sensitive active cladding-based and absorption-based fiber sensors.

The IPM technology incorporates a specific type of grating structure within a waveguide structure to couple bound modes into interfacial propagating modes. As is known to those skilled in the art, a Bragg grating couples light signals in an optical fiber, from a forward propagating mode to a backward propagating mode, by reflecting a specific wavelength of light depending on the spatial periodicity structure of the grating as described, for example, in U.S. Pat. No. 5,563,967.

To produce PM's in an optical waveguide, the initial forward propagating bound mode can be coupled into a backward propagating interfacial mode with an effective index of refraction greater than the fiber core refractive index, i.e., $n_f > n_{core}$. This condition is satisfied whenever the Bragg grating period ($\Lambda$) is very short, typically less than 200 nm. In this region, up to half of the total IPM energy may be propagated in the fiber cladding.

DETAILED DESCRIPTION OF THE IN ON

Figure 1:
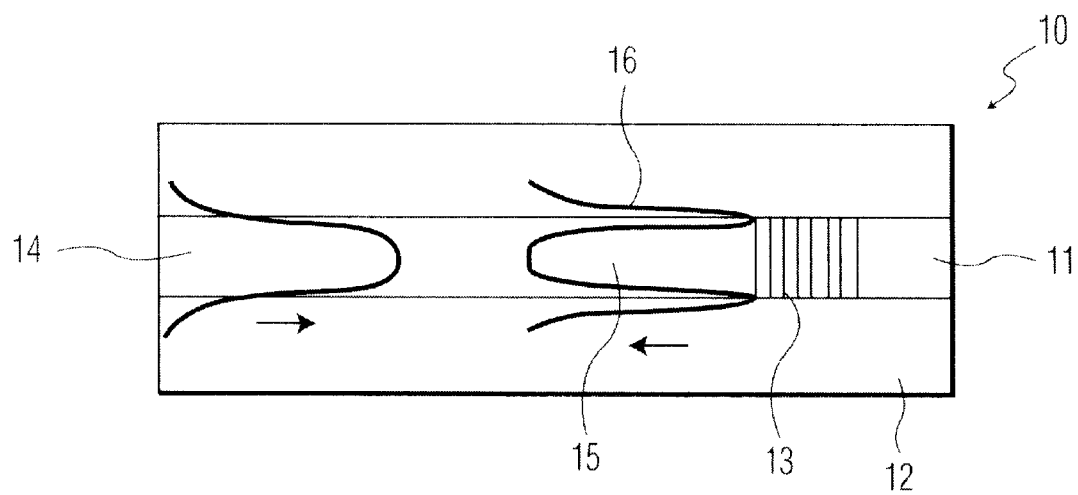
FIG. 1 is an illustrative view of the power distribution of an interfacial propagating mode in an optical waveguide.

FIG. 1 shows an interfacial propagating mode (IPM) optical fiber waveguide 10 comprised of an inner fiber core 11, a surrounding outer cladding medium 12, and a low period optical grating 13. The inner core 11 has a higher refractive index than the outer cladding 12 such that light 14 propagates as a forward bound mode within the inner core 11. The forward propagating light energy 14 incident on the grating 13, is reflected or coupled into a backward propagating mode or IPM 15 by the periodic structure or grating 13 with a higher percentage of the reflected energy 16 being propagated in the cladding medium 12.

Figure 2:
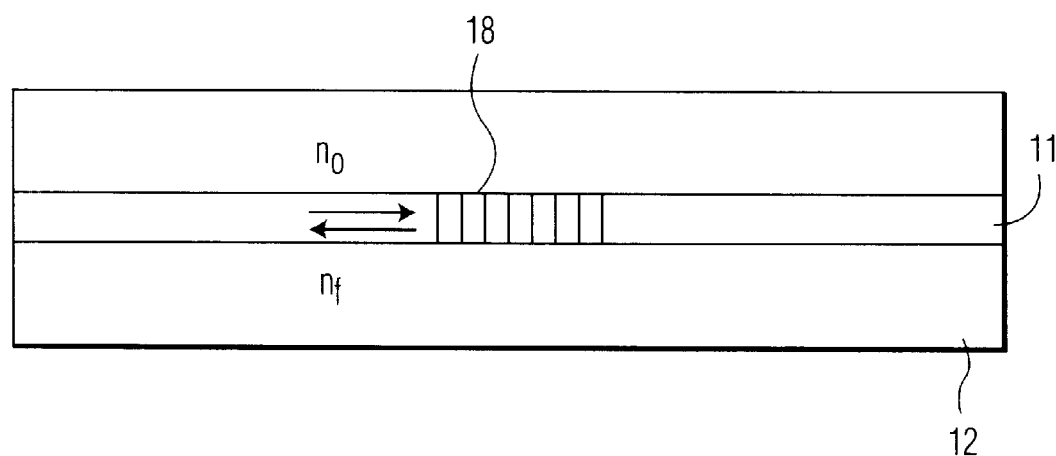
FIG. 2 is an illustration of modal coupling in an optical fiber.

IPM's can be generated by coupling light from a bound mode using an optical fiber Bragg grating 18, as shown in FIG. 2. The period of the Bragg grating required can be determined by using the phase matching condition equation $$\beta_0 - \beta_f = 2\pi/\Lambda \qquad (1)$$

where $\Lambda$ is the grating period, $\beta_0$ is the propagation constant of the initial forward propagating mode and $\beta_f$ is the propagation constant of the final coupled propagating mode. If we relate the propagation constant in terms of the effective index of refraction where $\beta = kn$, the phase matching condition equation (1) becomes $$\Lambda = \lambda/(n_0 - n_f) \qquad (2)$$

In equation (2), $\Lambda$ is the Bragg grating period, $\lambda$ is the wavelength of the propagated signal, $n_0$ is the initial effective index of refraction and $n_f$ is the effective index of refraction of the final mode.

Figures 3, 4:
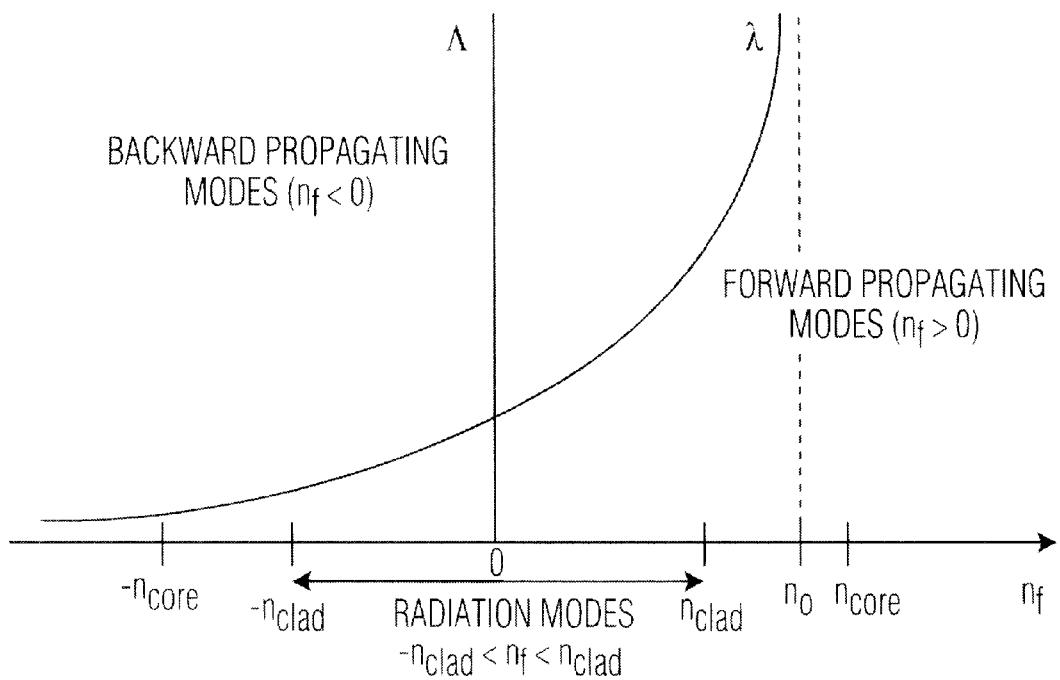
FIG. 3 is a plot of the grating period versus the effective index of refraction of a waveguide mode.
FIG. 4 is a table of relative characteristics of optical bound modes and IPM's.

FIG. 3 shows a generic plot of equation (2) where it can be seen that in the region where $n_f > 0$, coupled modes propagate in the forward direction and in the region where $n_f < 0$, coupled modes propagate in the backward direction. These two regions can be further subdivided into five different regions as follows:

1. For $n_f > n_0$, the grating period is negative and no mode can be coupled because a negative grating period has no physical meaning
2. Within the region $n_{clad} < n_f < n_0$, the initial mode couples into a forward propagating bound mode. This interval corresponds to structures called long period gratings
3. Within the interval $-n_{clad} < n_f < n_{clad}$, the initial mode couples into a forward and backward radiation mode. These modes are generated by medium period gratings
4. Within the interval $-n_{clad} > n_f > -n_{core}$, the initial mode couples into backward propagating bound modes and regular grating periods are required
5. In the region where $n_f < -n_{core}$, the initial bound mode couples into a backward propagating interfacial mode (IPM). Shorter period gratings, typically less than 200 nm, can be used to couple modes within this region.

In addition, as illustrated in FIG. 4, the power characteristic of the forward propagating waveguide bound mode of a regular bound mode fiber is distributed mostly within the core of the waveguide whereas, for an IPM, most of the power is at the core and cladding interface. Consequently, an IPM can produce a higher power distribution in the cladding than a regular bound mode.

Figure 5:
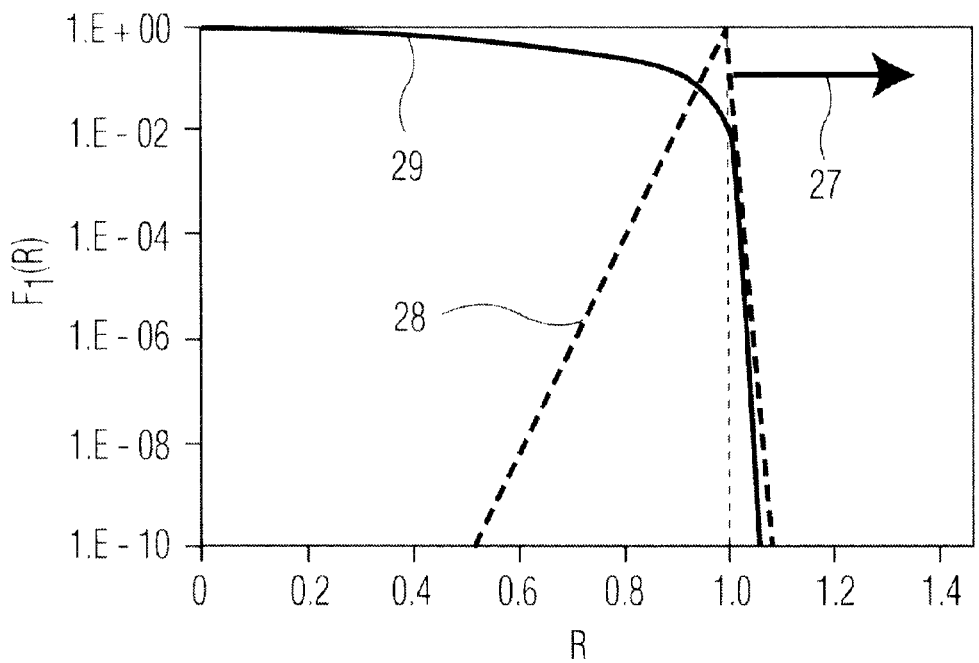
FIG. 5 is a graph comparing the power distribution of bound modes and IPM's.

FIG. 5 is a plot of the radial portion of the electric field distribution $F_1(R)$ and normalized fiber radius R for two different kinds of bound modes. As shown in FIG. 5, the fraction of power in the evanescent wave region of a fiber 27 is higher for an interfacial propagating bound mode 28 than for a regular bound mode 29.

Figure 6:
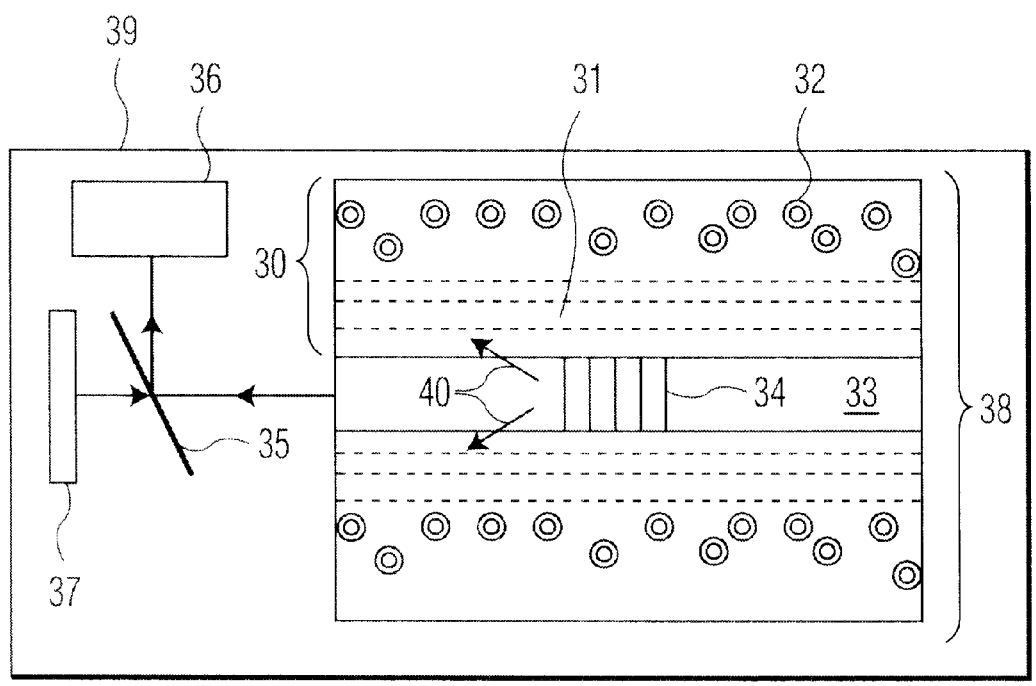
FIG. 6 is an illustrative view of an IPM fiber optic sensor.

FIG. 6 shows an optical fiber sensor apparatus 39, according to one embodiment of the invention, for detecting the presence of gaseous or chemical analytes. The sensor 39 comprises a broadband light source 37, a 50/50 beam splitter 35, a detector 36 and an optical waveguide 38 having a fiber core 33, an absorptive cladding 30, an indicator dye 31, and a low period Bragg grating 34. The absorptive cladding is doped with the indicator dye for changing the absorption properties of the cladding in response to the presence of an analyte 32 in the cladding 30.

In operation, light from the broadband source 37 is injected into the waveguide 38 through the beam splitter 35. An IPM low period Bragg grating 34, responsive to the wavelength of light absorbed by the indicator dye 31, is selected to couple waveguide core-bound modes into backward propagating interfacial bound modes whereby the evanescent field of light 40 in the fiber core 33 interacts with the indicator dye 31 in the absorptive cladding 30.

As is known in the art, when an analyte 32 permeates the cladding 30, molecules of the analyte interact with molecules of the indicator dye 31 causing a change in the absorption properties of the cladding 30 and altering the output of the waveguide 38. The output of the waveguide 38 is transmitted by the beam splitter 35 to the detector 36 to indicate the presence of a measured An optical spectrum analyzer is a typical type of detector that can be used in sensor applications.

Because interfacial propagating modes have more power in the cladding than conventional bound modes, greater changes in waveguide output can be produced, resulting in enhanced sensor sensitivity. Conventional fiber sensors have only a small percentage, typically one percent, of transmitted light energy dispersed in the cladding region of the fiber. Using interfacial mode propagation, up to fifty percent of the transmitted power can be propagated in the cladding, providing a sensor having many times the sensitivity of conventional devices.

The various features of novelty that characterize this invention are pointed out with particularity in the claims annexed to and forming a part of this disclosure.

What is claimed is:

1. Apparatus for transmitting an optical signal comprising an optical fiber waveguide having an inner core and an outer cladding, said core and cladding having first and second indices of refraction respectively, said first index of refraction being greater than said second index of refraction, said waveguide including a periodic grating structure for coupling a forward propagating bound mode into a backward propagating mode, said grating structure having a spatial periodicity such that the effective index of refraction of said backward propagating mode is greater than said core refractive index; whereby a substantial portion of said optical signal is propagated in said outer cladding.

2. Apparatus as in claim 1, whereby said periodic grating structure is a Bragg grating having a grating period selected in the region where $n_{f<-ncore}$ in accordance with the following expression:

$$\Lambda = \frac{\lambda}{n_0 - n_f}$$

wherein $\Lambda$ is the selected grating period, $\lambda$ is the wavelength of said optical signal, $n_0$ is the effective index of refraction of said forward propagating mode, $n_f$ is the effective index of refraction of said backward propagating interfacial mode and $n_{core}$ is the core refractive index.

3. Apparatus as in claim 2, wherein said selected grating period is less than 200 nm.

4. Apparatus as in claim 1, whereby up to one half of the energy in said backward propagating mode is propagated in said outer cladding.

5. Sensor apparatus for detecting the presence of a gaseous or chemical analyte by increasing light absorption in the cladding of an optical fiber comprising:

light source means for injecting light into said optical fiber, detection means for measuring the optical output of said fiber, an optical fiber waveguide having an inner core and an outer cladding, said cladding including light absorbing material, said core and cladding having first and second indices of refraction respectively, said first index of refraction being greater than said second index of refraction, said light absorbing material responsive to molecules of said analyte for changing the absorption properties of said cladding, said waveguide including a periodic grating structure for coupling a forward propagating bound mode into a backward propagating mode, said grating structure having a spatial periodicity such that the effective index of refraction of said backward propagating mode is greater than said core refractive index whereby a substantial portion of said optical signal is absorbed by said outer cladding.

6. Apparatus as in claim 5, wherein said light absorbing material is fluorescent.

7. Apparatus as in claim 5, whereby said periodic grating structure is a Bragg grating having a grating period selected in the region where $n_f<-n_{core}$ in accordance with the following expression:

$$\Lambda = \frac{\lambda}{n_0 - n_f}$$

wherein $\Lambda$ is the selected grating period, $\lambda$ is the wavelength of said optical signal, $n_0$ is the index of refraction of said forward propagating mode, $n_f$ is the effective index of refraction of said backward propagating interfacial mode and $n_{core}$ is the core refractive index.

8. Apparatus as in claim 7, wherein said grating period is less than 200 nm.

* * * * *